(12) United States Patent (10) Patent No.: US 8,008,289 B2
Grainger et al. (45) Date of Patent: Aug. 30, 2011

(54) α-AMINOCYCLOLACTAM LIGANDS FOR G-PROTEIN COUPLED RECEPTORS

(75) Inventors: David J. Grainger, Cambridge (GB); David John Fox, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 532 days.

(21) Appl. No.: 11/574,656

(22) PCT Filed: Aug. 10, 2005

(86) PCT No.: PCT/GB2005/003134
§ 371 (c)(1),
(2), (4) Date: Dec. 17, 2007

(87) PCT Pub. No.: WO2006/024815
PCT Pub. Date: Mar. 9, 2006

(65) Prior Publication Data
US 2008/0161283 A1 Jul. 3, 2008

(30) Foreign Application Priority Data
Sep. 2, 2004 (GB) .................................. 0419517.8

(51) Int. Cl.
C07D 453/06 (2006.01)
C07D 487/08 (2006.01)
A61K 31/439 (2006.01)
A61K 31/55 (2006.01)
(52) U.S. Cl. ................... 514/212.05; 514/299; 540/520; 546/183
(58) Field of Classification Search ............. 514/212.05, 514/299; 540/520; 546/183
See application file for complete search history.

(56) References Cited

U.S. PATENT DOCUMENTS
6,395,282 B1 5/2002 Kende et al.
2008/0076755 A1 3/2008 Grainger FOREIGN PATENT DOCUMENTS
DE 10305922 3/2004
JP 10265761 10/1998
WO WO 97/017362 A1 5/1997
WO WO 99/12968 A2 3/1999
WO WO 00/42071 A2 7/2000
WO WO-2005053702 6/2005
WO WO-2005077900 8/2005
WO WO2006/018609 A2 2/2006

OTHER PUBLICATIONS

"International Search Report in Appln No. PCT/GB2005/003134", (Dec. 13, 2005),5 pgs.
Davidson, B S., "Isolation and synthesis of caprolactins A and B, new caprolactams from a marine bacterium", *Tetrahedron*, 49(30),(1993),6569-6574.

Fox, Daniel J., "Design, Synthesis, and Preliminary Pharmacological Evaluation of N-Acyl-3-aminoglutarimides as Broad-Spectrum Chemokine Inhibitors in Vitro and Anti-inflammatory Agents in Vivo", *J. Med. Chem.*, 45, (2002),360-370.
Grainger, David J., et al., "Broad spectrum chemokine inhibitors related to NR58-3.14.3", *Mini-Reviews in Medicinal Chemistry*, 5(9), (2005),825-32.
"International Preliminary Report on Patentability for related PCT Application No. PCT/GB2005/003134", (Mar. 15, 2007), 9 pgs.
"Search Report Under Section 17 for GB0419517.8", (Nov. 29, 2004), 1 pg.
Fox, David J., et al., "Identification of 3-(Acylamino)azepan-2-ones as Stable Broad-Spectrum Chemokine Inhibitors Resistant to Metabolism in Vivo", *J. Med. Chem.*, 48, (2005), 867-874.
Fox, David J., et al., "Supporting Information—Identification of 3-(acylamino)azepan-2-ones as Stable Broad-Spectrum Chemokine Inhibitors (BSCI) Resistant to Metabolism in vivo", (2005), S1-S6.
Fetzion et al., Synthese dans las serie d'alcoyl-4 aza-2 bicyclo-(2,2,2) octane, Bull. Soc. Chim. Fr. (1969) No. 1, pp. 194-197.
Gould, "Salt selection for basic drugs", Int. J. Pharm. (1986), 33, 201-217. Weiss et al., "Effects of Various Amides on a Rat Brain Puromycin-sensitive Aminopeptidase and on Induced Convulsions in Mice", Research Communications in Psychology, Psychiatry and Behavior (1992), 17(3-4), pp. 153-159.
Reckless et al., "Identification of Oligopeptide Sequences which Inhibit migration induced by a wide range of chemokines", Biochem J. (1999) 340:803-811.

(Continued)

*Primary Examiner* — Bruck Kifle
(74) *Attorney, Agent, or Firm* — VLP Law Group LLP; Richard G. A. Bone

(57) ABSTRACT

The invention relates to the generation of a library of compounds enriched in agonist and antagonists for members of the G-protein coupled class of receptors (GPCRs). The library contains compounds of general formula (I) wherein y is any integer from 1 to 8; z is one integer from 0 to 8 with the proviso that y and z cannot simultaneously be 1; X is —CO—$(Y)_k$—$(R^1)_n$ or $SO_2$—$(Y)_k$—$(R^1)_n$; k is 0 or 1; y is a cycloalkyl or polycyloalkyl group (such as an adamantyl, adamantanemethyl, bicyclooctyl, cyclohexyl, cyclopropyl group); or y is a cycloalkenyl or polycycloalkenyl group; each $R^1$ is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms; or each $R^1$ is independently selected from fluoro, chloro, bromo, iodo, hydroxy, oxyalkyl, amino, aminoalkyl, aminodialkyl, charged aminotrialkyl, or carboxylate radical; and n is any integer from 1 to m, where m is the maximum number of substitutions permissible on the cyclo-group Y; or alternatively $R^1$ may be selected from a peptido radical, for example having from 1 to 4 peptidic moieties linked together by peptide bonds (for example a peptido radical of 1 to 4 amino acid residues).

(I)

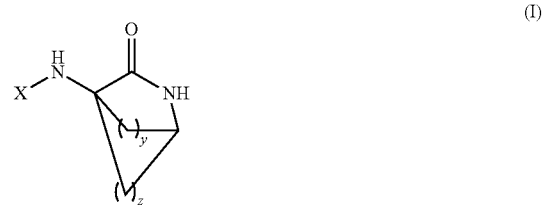

23 Claims, No Drawings

OTHER PUBLICATIONS

Fox et al, "Design, Synthesis, and Preliminary Pharmacological Evaluation of N-Acyl-3-aminoglutarimides as Broad-Spectrum Chemokine Inhibitors in Vitro and Anti-inflammatory Agents in Vivo", J. Med. Chem. 45(2002) 360-370.

Grainger et al., "Broad-spectrum chemokine inhibitors (BSCIs) and their anti-inflammatory effects in vivo", Biochem. Pharm. 65 (2003) 1027-1034.

Boyle, et al., "Asymmetric Transformation of alpha-Amino-epsilon-caprolactam, a Lysine Precursor", J. Org. Chem., vol. 44, (1979), pp. 4841-4847.

Kuo, et al., "Calcium-dependent protein kinase: Widespread occurrence in various tissues and phyla of the animal kingdom and comparison of effects of phospholipid, calmodulin, and trifluoroperazine", Proc. Natl. Acad. Sci. USA, vol. 77, pp. 7039-7043, (1980).

Rezler et al., "Preparation, Characterization, DNA Binding, and in Vitro Cytotoxicity of the Enantiomers of the Platinum (II) Complexes N-Methyl-, N-Ethyl- and N,N-Dimethyl-(R)- and -(S)-3-aminohexahydroazepinedichloroplatinum(II)", J. Med. Chem., 40, 3508-3515, (1997).

International Search Report for PCT/GB05/03139 (WO2006/018609) dated Jan. 25, 2006.

IPRP for PCT/GB05/03139 (WO2006/018609) dated Feb. 20, 2007.

Search Report for GB0418375.2, dated Nov. 29, 2004.

Asao, et al., "Structure of Reaction Products of 5-Nitrosotropolone and Arylamine", Bull. Chem. Soc. Japan, vol. 63, (1990), pp. 3089-3095.

Hughes et al., "Total Synthesis of Cyclobutane Amino Acids from Atelia herbert smithii", J. Org. Chem., (1988), vol. 53, pp. 4793-4796.

Pacquette et al., "Addition Reactions of Uniparticulate Electrophile Chlorosulfonyl Isocyanate to Highly Strained Bicyclic Hydrocarbons", J. Am. chem. Soc., vol. 93, pp. 4503-4508, (1971).

Zahn et al., Chemische Berichte, vol. 91, pp. 1359-1371, (1958).

α-AMINOCYCLOLACTAM LIGANDS FOR G-PROTEIN COUPLED RECEPTORS

This application is a U.S. National Stage Filing under 35 U.S.C. 371 from International Application No. PCT/GB2005/003134, filed Aug. 10, 2005 and published in English as WO 2006/024815 A1 on Mar. 9, 2006, which claims the benefit under 35 U.S.C. §119 of United Kingdom application serial number 0419517.8, filed Sep. 2, 2004, which applications and publication are incorporated herein by reference.

The invention relates to the generation of a library of compounds enriched in agonist and antagonists for members of the G-protein coupled class of receptors (GPCRs).

Members of the G-protein coupled receptor (GPCR) class of membrane proteins (also known as seven-transmembrane spanning or 7TM receptors and serpentine receptors) mediate cellular signalling in response to a very wide variety of extracellular signals, including hormones, neurotransmitters, cytokines and even environmental substances such as odours and tastes. In response to the ligand interacting with the extracellular portion of the receptor (most usually the N-terminal tail of the receptor protein), the receptor is converted temporally to an activated state (this conversion is usually designated R+L→R*L where R is the inactive receptor, R* is the activated receptor and L is the ligand).

The activated (or R*) conformation of the receptor is then able to interact with a member of the G-protein family. The G-proteins are a large family of trimeric intracellular proteins which bind guanine nucleotides. On interacting with the activated receptor (probably by a mechanism called "collisional coupling") the G-protein exchanges a bound guanosine diphosphate (GDP) for a guanosine triphosphate (GTP). In this GTP-bound form the G-protein trimer dissociates, yielding a free Gα subunit, and a βγ dimer. Both the Gα and βγ subunits can then participate in further signalling cascades. For example, the Gα subunit can activate the adenylate cyclase (AC) enzyme, which generates cyclic adenosine monophospate (cAMP) from adenosine triphosphate. The βγ subunit can activate members of the PI-3-kinase family of enzymes. Ultimately, these signals can result in modulation of almost every aspect of cell behaviour, from contraction to motility, metabolism to further signalling.

The signal, once activated, is then slowly turned off by a number of mechanisms. The GTP associated with the Gα subunit is hydrolysed back to GDP, resulting in the reassociation of the Gα and βγ subunits to form the inactive trimeric GDP-bound G-protein. The GPCR itself also becomes phosphorylated on the intracellular C-terminus, preventing further interaction with G-proteins. Eventually, the bound ligand may also dissociate.

This generic signalling pathway is so central and ubiquitous in mammalian physiology that as many as 40% of licensed pharmaceuticals have a GPCR among their molecular targets. Similarly, bacteria have evolved to target G-protein signalling in order to disrupt host physiology and immunity: *Vibrio cholerae* (the organism responsible for cholera), for example, makes a protein known as cholera toxin which irreversibly inhibits the Gα subunit of a widely distributed G-protein called $G_s$. Similarly, *Bordetella pertussis* (the organism responsible for Whooping Cough) makes a protein known as Pertussis toxin which has a similar effect on a different G-protein, $G_i$.

One approach to identifying pharmaceuticals which will modulate GPCR signalling has been to screen very large random compound libraries for the ability to interfere with ligand binding to membrane preparations containing recombinant or purified GPCRs. In such high throughput screens, various methods have been adopted to facilitate the detection of binding. For example, in scintillation proximity assays, the binding of a radiolabelled ligand to the receptor brings the radionuclide into proximity with a scintillant molecule bound to the receptor—as the nuclide decays, light is emitted which can be detected and quantified. Alternatively, the ligand can be fluorescently labelled and the binding detected by fluorescence polarisation (dependent on the reduced rotational degress of freedom of the fluorescent tag when the ligand is immobilised on binding to the receptor).

While these techniques have been successful in some instances, and yielded lead compounds which have subsequently been developed as human pharmaceuticals (for example, the $5HT_3$ receptor antagonist Ondansetron, used to treat migraine headaches), there remain large numbers of GPCRs for which few, if any, suitable non-peptide agonist or antagonist compounds have been identified, despite intensive screening across the pharmaceutical industry. For example, there are few specific non-peptide antagonists for the chemokine receptor family of GPCRs, and no agonists. Since chemokines play a central role in immune regulation, such molecules would be expected to be extremely valuable pharmaceuticals with immunomodulatory properties useful in treating a wide range of diseases with an inflammatory component.

Two factors limit the likely success of random screening programmes: firstly, there is a very large compound space to be screened, and even with the best available high throughput technology and the best combinatorial chemistry approaches to generating diverse libraries, only a small fraction of all possible molecular structures can be investigated. Secondly, even when leads have been successfully identified the core pharmacophores are often not suitable for use in vivo—the lead compound and its analogs may be simply too toxic.

Another major problem with such "negative screening" paradigms (where you detect the ability of the test library to block binding of a labelled ligand) is that most of the leads identified are receptor antagonists. Few of the leads have any agonist activity (as expected—agonist activity requires the ability to bind to and then convert the receptor to the activated conformation, whereas antagonist actively merely requires the ability to bind to the receptor or ligand in such a way as to prevent their interactions) and generating analogs of the initial antagonist leads to convert them to agonists is a "hit and miss" affair with very low success rates.

One approach to circumventing this problem would be to replace the random compound library with a library of molecular structures preselected to contain a high proportion of GPCR binding compounds. Such a library would also ideally include both agonists and antagonists in similar proportion so that either could be readily located. Ideally, also, the basic molecular structures used in the library would be non-toxic.

Whether or nor real libraries can be constructed which approximate these ideal properties is not at all clear. If they do, it will require the existance of a putative "ideal" GPCR substrate which would interact with many different GPCRs irrespective of their natural ligand preferences. By varying the substitution of this idealised substrate it may then be possible to impart selectivity for one receptor in the class over all the others.

Here we describe an "ideal" GPCR substrate which can be used as a three-dimensional skeleton that can be variously substituted to generate agonists and/or anatagonists at a range of different GPCRs. The invention also provides for the preparation of a library of said substituted compounds to be applied in a screening process in order to generate GPCR ligands with any prescribed set of specificities. In this way, it is now possible to "dial up" a GPCR ligand with a known set of properties (for example, a ligand which has agonist activity at dopamine D2 receptors at the same time as antagonist activity at serotonin $5HT_{1a}$ (receptors). In contrast, identifying such mixed ligands serendipitously from random libraries is a very rare event.

The invention provides compounds and salts thereof of general formula (I)

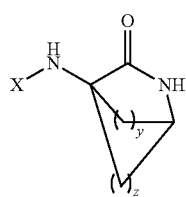

(I)

wherein
y is any integer from 1 to 8;
z is any integer from 0 to 8 with the proviso that y and z cannot simultaneously be 1;
X is —CO—$(Y)_k$—$(R^1)_n$ or $SO_2$—$(Y)_k$—$(R^1)_n$;
k is 0 or 1
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each $R^1$ is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each $R^1$ is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively $R^1$ may be selected from a peptido radical, for example having from 1 to 4 peptidic moieties linked together by peptide bonds (for example a peptido radical of 1 to 4 amino acid residues).

This class of compounds are described as α-aminocyclolactams. The key structural features of the molecules are the lactam amide in a cycloalkyl ring system, with an amino group attached to the carbon atom next to the lactam carbonyl group (termed the α-carbon).

The terms "α-aminocyclolactam" and "cycloalkyl ring system" as used herein cover both mono-cyclic and bicyclic rings;
Where z=0 in Formula (I) the compounds are α-aminomonocyclolactams;
Where z=1-8 in Formula (I) the compounds are α-aminobicyclolactams.

The α-carbon of α-aminocyclolactams may be asymmetric (where y< >z in the general formula (I)) and consequently, some of the compounds according to the present invention have two possible enantiomeric forms, that is, the "R" and "S" configurations. The present invention encompasses the two enantiomeric forms and all combinations of these forms, including the racemic "RS" mixtures. With a view to simplicity, when no specific configuration is shown in the structural formulae, it should be understood that the two enantiomeric forms and their mixtures are represented.

The compounds of general formula (I) are N-substituted α-aminocyclolactams, or their pharmaceutically acceptable salts. The N-substitutent is either a carbon amide or a sulfonamide. The geometry of the carbon atom next to the carbonyl of the carbon amide or the sulfoyl group of the sulfonamide (the "key" carbon) may be important for the bioactivity of the molecule. The nature of the N-substituent may be such that the ring or rings of Y constrain the bond angles at the "key"-carbon to be essentially tetrahedral (i.e. sp3 hybrid bonds).

Any substituent $R^1$ may be a substituent at any permissible position on the ring or rings of the cyclo-group Y. In particular it is to be noted that the invention includes compounds in which the "key carbon" is both part of the cyclo group and is itself substituted. The definition of $(R^1)_n$ encompasses compounds of the invention with no substitution (i.e. $R^1$=hydrogen), compounds of the invention with mono substitution (i.e. $R^1$ is not hydrogen and n=1), and also multiple substitution (i.e. at least two $R^1$ groups are not hydrogen and n=2 or more).

The invention also provides pharmaceutical compositions comprising, as active ingredient, a compound of general formula (I), or a pharmaceutically acceptable salt thereof, and at least one pharmaceutically acceptable excipient and/or carrier:

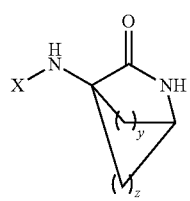

(I)

wherein
y is any integer from 1 to 8;
z is any integer from 0 to 8 with the proviso that y and z cannot simultaneously be 1
X is —CO—$(Y)_k$—$(R^1)_n$ or $SO_2$—$(Y)_k$—$(R^1)_n$;
k is 0 or 1
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each $R^1$ is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each $R^1$ is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively $R^1$ may be selected from a peptido radical, for example having from 1 to 4 peptidic moieties linked together by peptide bonds (for example a peptido radical of 1 to 4 amino acid residues).

By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention also provides the use of a compound of general formula (I), or a pharmaceutically acceptable salt thereof, for the preparation of a medicament intended to modulate the activity of one or more members of the G-protein coupled receptor (GPCR) class:

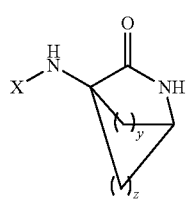

(I)

wherein
y is any integer from 1 to 8;
z is any integer from 0 to 8 with the proviso that y and z cannot simultaneously be 1
X is —CO—(Y)$_k$—(R$^1$)$_n$ or SO$_2$—(Y)$_k$—(R$^1$)$_n$;
k is 0 or 1
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each R$^1$ is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each R$^1$ is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively R$^1$ may be selected from a peptido radical, for example having from 1 to 4 peptidic moieties linked together by peptide bonds (for example a peptido radical of 1 to 4 amino acid residues).

The invention provides compounds, compositions and uses of the compounds of general formula (I) or their pharmaceutically acceptable salts, wherein the R$^1$ radical has a "key" carbon which is di-substituted with the same or different groups selected from: alkyl, haloalkyl, alkoxy, haloalkoxy, alkenyl, alkynl and alkylamino radicals.

The invention provides compounds, compositions and uses wherein the "key" carbon is chiral.

The invention provides compounds, compositions and uses wherein the "key" carbon has sp3 hybridised bonds.

The invention provides compounds, compositions and uses wherein the "key" carbon has essentially tetrahedral bond angles.

The compounds of general formula (I) when used in the invention, or their salts, may be such that the ring or rings of Y constrain the bond angles at the "key" carbon to be essentially tetrahedral (i.e. sp3 hybrid bonds).

In an alternative embodiment of the invention, general formula (I) is modified such that the C3-C7 alkyl bridge —(CH$_2$)$_y$— is replaced by a bridging group independently selectable from the group consisting of alkenyl, haloalkyl, alkylamino, alkylaminoalkyl, alkylaminodialkyl, charged alkylaminotrialkyl, charged alkylcarboxylate and alkylhydroxy moieties having a carbon chain length of from 1 to 8.

The invention provides a use, composition or compound wherein y and z are the same integer from 1-8, whereby the bicyclolactam ring is non-chiral.

The invention provides a use, composition or compound wherein y and z are not the same integer from 1-8, whereby the bicyclolactam ring is chiral.

The invention provides a use, composition or compound wherein z is 3 and y is 1 or 2 or 4-8, whereby the compound contains a lactam ring which is seven membered.

The invention provides a use, composition or compound wherein z is 2 and y is 1 or 3-8, whereby the compound contains a lactam ring which is 6 membered.

Examples of compounds of general formula (I) and their salts according to the present invention are:
4-(Adamantane-1-carbonylamino)-3-oxo-2-aza-bicyclo [2.2.2]octane
5-(Adamantane-1-carbonylamino)-10-oxo-9-aza-bicyclo [3.3.2]decane
4-(2',2'-dimethyldodecanoylamino)-3-oxo-2-aza-bicyclo [2.2.2]octane
5-(2',2'-dimethyldodecanoylamino)-10-oxo-9-aza-bicyclo [3.3.2]decane
and the salts thereof.

The invention also provides the sulfonamide analogues of the exemplified compounds: i.e. the sulfonyl-α-aminocyclolactam equivalents of the compounds of Formula (I).

The invention includes compounds, compositions and uses thereof as defined, wherein the compound is in hydrated or solvated form.

The amide and sulfonamide derivatives of α-aminocyclolactams described here are functional GPCR agonists. They are stable in human serum and consequently have excellent pharmacokinetic properties; they are orally bioavailable; they are highly potent GPCR agonists; their administration is not associated with any significant acute toxicity at the doses necessary to achieve a maximal therapeutic effect. Taken together, these properties suggest that amide and sulfonamide derivatives of α-aminocyclolactams represent a series of compounds enriched in GPCR agonist and antagonist properties The core consisting of the "key" carbon, the carbonyl or sulfonyl group, the α-amino group and the cyclolactam system (particularly the constrained bicyclolactam ring system) represents an exampe of an "ideal" GPCR ligand. By varying the substitution of this core, it is possible to generate GPCR agonists and antagonists with a wide range of desirable properties much more readily than by screening random compound libraries.

As a result, the invention also provides for a library consisting of two or more members of the class of compounds designated by general formula (I), such that the library may be screened to identify a molecule with a particular desirable set of properties with regard to modulating signalling at one (or more) GCPRs. The said library would then be screened for antagonist or agonist activity at the said GPCR(s) using methods well known in the art. For example, the library may be screened for the ability of individual library elements to block the binding of a radiolabelled GPCR ligand to a membrane preparation containing recombinant or purified GPCR. Alternatively, the library may be screened for the ability of individual library elements to stimulate cAMP production in cells expressing a recombinant GPCR.

The invention also provides a method of treatment, amelioration or prophylaxis of the symptoms of disease or condition selected from the group consisting of hypertension, atherosclerosis, asthma, obesity, neurodegenerative disorders, autoimmune disorders or psychopathic disorders by the administration to a patient of an effective amount of a compound, composition or medicament of the invention designed to modulate GPCR activity.

DEFINITIONS

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 1 to 20 carbon atoms specified in respect of (inter alia) formula I is intended to include all integers between 4 and 20 and all sub-ranges of each combination of upper and lower numbers, whether exemplified explicitly or not.

As used herein, the term "comprising" is to be read as meaning both comprising and consisting of: Consequently, where the invention relates to a "pharmaceutical composition comprising as active ingredient" a compound, this terminology is intended to cover both compositions in which other active ingredients may be present and also compositions which consist only of one active ingredient as defined.

The term "peptidic moieties" used herein is intended to include the following 20 naturally-occurring proteogenic amino acid residues:

| SYMBOL: | MEANING |
|---|---|
| Ala | Alanine |
| Cys | Cysteine |
| Asp | Aspartic Acid |
| Glu | Glutamic Acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |

-continued

| SYMBOL: | MEANING |
|---|---|
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Modified and unusual amino acid residues, as well as peptido-mimetics, are also intended to be encompassed within the definition of "peptidic moieties".

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the invention and should in no way be considered to limit the scope of the invention.

EXAMPLES

General Procedure for the Synthesis of the Starting Compounds

The hydrochlorides of (R) and (S)-3-amino-caprolactam, and the hydro-pyrrolidine-5-carboxylates of (R,R) and (S,S)-3-amino-caprolactam were synthesised according to literature (cf. Boyle et al., *J. Am. Chem. Soc.* (1979), 44, 4841-4847; Rezler et al., *J. Med. Chem.* (1997), 40, 3508-3515).

Example 1

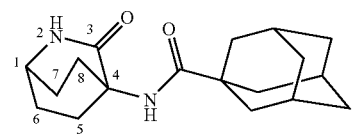

4-(Adamantane-1-carbonylamino)-3-oxo-2-aza-bicyclo[2.2.2]octane

Example 2

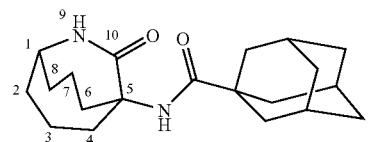

5-(Adamantane-1-carbonylamino)-10-oxo-9-aza-
bicyclo[3.3.2]decane

Example 3

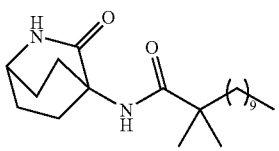

4-(2',2'-dimethyldodecanoylamino)-3-oxo-2-aza-
bicyclo[2.2.2]octane

Example 4

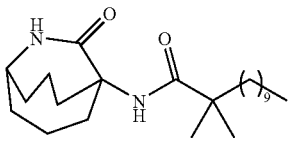

5-(2',2'-dimethyldodecanoylamino)-10-oxo-9-aza-
bicyclo[3.3.2]decane

Pharmacological Study of the Products of the Invention
Principle of the Assays
A: GPCR Antagonism In principle, a compound of the invention can be tested for antagonist activity at a given GPCR by exposing the receptor to a labelled ligand under appropriate conditions for binding, in the absence and presence of various concentrations of the test compound. The amount of label associated with the receptor is then quantitated. If the test compound is able to compete with the labelled ligand for binding then the amount of label associated with the receptor will decrease with increasing concentration of the test compound. From the plot of ligand bound against test compound concentration it is possible to estimate the binding affinity of the test compound to the receptor.

Such an assay therefore requires:

(1) A source of the GPCR of interest. The sequence of every member of the GPCR superfamily from humans is now available from the human genome sequence. Such sequences can be cloned into a suitable vector and expressed in a suitable cell type (for example, Jurkat T cells which are already known to express virtually no endogenous GCPRs with the exception of the chemokine receptor CXCR4). After selection using an antibiotic appropriate to the vector used, stable cell lines expressing high levels of the chosen GPCR can be established.

Membrane fractions from cell lines expressing the chosen GPCR can be prepared using a range of methods well known in the art. For example, according to Kuo et al. (Proc. Natl. Acad. Sci. USA (1980) 77:7039), the cells may be resuspended in 25 mM HEPES buffer pH7.5 containing 0.25M sucrose, 2.5 mM $MgCl_2$, 2.5 mM EGTA and 50 mM β-mercaptoethanol, as well as protease inhibitors such as PMSF and leupeptin and split open using a Dounce homogeniser. The suspension is then subjected to centrifugation at 120×g to pellet unbroken cells and large cellular fragments, and the supernatant containing small membrane fragments and cytosolic components is retained. This supernatant is then subjected to ultracentrifugation at 100,000×g, producing a pellet of membrane fragments enriched in the chosen GPCR. The pellet is resuspended in an appropriate binding buffer, and the total protein concentration determined using, for example, a commercially available protein assay such as Coomassie Plus (Pierce). The membrane preparation can be adjusted in volume to yield a standardised total protein concentration, for example of 1 mg/ml. The standardised preparation can be stored at −85° C. in aliquots until required.

(2) A labelled ligand with high affinity for the chosen GPCR. Suitable ligands for most GPCRs are well known in the literature. Such ligands may be the natural ligand for the receptor (for example, dopamine) or it may be a pharmacological tool (such as domperidone). A list of suitable ligands for a wide range of commonly investigated GPCRs is provided in Table 1, but it will be obvious to those skilled in the art that other suitable ligands exist for many of these receptors. Ligands most useful for this purpose will have an affinity constant for binding to the chosen receptor of at least 1 μM, and preferably less than 100 nM, and more preferably less than 10 nM.

TABLE 1

| Receptor | Radioligand | Conc (nM) | Competitor | Conc (μM) |
| --- | --- | --- | --- | --- |
| Adenosine $A_1$ | [$^3$H]DPCPX | 1 | DPCPX | 1 |
| Adenosine $A_2$ | [$^3$H]CGS 21680 | 6 | NECA | 10 |
| Adenosine $A_3$ | [$^{125}$I]AB-MECA | 0.1 | IB-MECA | 1 |
| $\alpha_1$-adrenoceptor | [$^3$H]prazosin | 0.25 | prazosin | 0.5 |
| $\alpha_2$-adrenoceptor | [$^3$H]RX 821002 | 0.5 | (−)-epinephrine | 100 |
| $\beta_1$-adrenoceptor | [$^3$H](−)-CGP 12177 | 0.15 | alprenolol | 50 |
| $\beta_2$-adrenoceptor | [$^3$H](−)-CGP 12177 | 0.15 | alprenolol | 50 |
| Angiotensin $AT_1$ | [$^{125}$I][sar$^1$,ile$^8$]-AII | 0.05 | angiotensin II (AII) | 10 |
| Angiotensin $AT_2$ | [$^{125}$I]CGP 42112A | 0.05 | angiotensin II (AII) | 1 |
| Central BZD | [$^3$H]flunitrazepam | 0.4 | diazepam | 3 |
| Peripheral BZD | [$^3$H]PK 11195 | 0.2 | PK 11195 | 10 |
| Bombesin (ns) | [$^{125}$I][Tyr$^4$]bombesin | 0.01 | bombesin | 1 |
| Bradykinin $B_2$ | [$^3$H]bradykinin | 0.2 | bradykinin | 1 |
| CGRP receptor | [$^{125}$I]hCGRPα | 0.03 | hCGRPα | 1 |
| Cannabinoid $CB_1$ | [$^3$H]WIN 55212-2 | 2 | WIN 55212-2 | 10 |
| Cholecystekinin A | [$^{125}$I]CCK-8 | 0.08 | CCK-8 | 1 |
| Cholecystekinin B | [$^{125}$I]CCK-8 | 0.025 | CCK-8 | 1 |
| Dopamine D1 | [$^3$H]SCH 23390 | 0.3 | SCH 23390 | 1 |
| Dopamine D2s | [$^3$H]spiperone | 0.3 | (+)-butaclamol | 10 |

TABLE 1-continued

| Receptor | Radioligand | Conc (nM) | Competitor | Conc (μM) |
|---|---|---|---|---|
| Dopamine D3 | [$^3$H]spiperone | 0.3 | (+)-butaclamol | 10 |
| Dopamine D4.4 | [$^3$H]spiperone | 0.3 | (+)-butaclamol | 10 |
| Dopamine D5 | [$^3$H]-SCH 23390 | 0.3 | SCH 23390 | 10 |
| Endothelin ET$_A$ | [$^{125}$I]endothelin-1 | 0.03 | endothelin-1 | 0.1 |
| Endothelin ET$_B$ | [$^{125}$I]endothelin-1 | 0.03 | endothelin-1 | 0.1 |
| GABA (ns) | [$^3$H]-GABA | 10 | GABA | 100 |
| Galanin GAL1 | [$^{125}$I]galanin | 0.03 | galanin | 1 |
| Galanin GAL2 | [$^{125}$I]galanin | 0.05 | galanin | 1 |
| IL8RB (CXCR2) | [$^{125}$I]IL-8 | 0.025 | IL-8 | 0.3 |
| CCR1 | [$^{125}$I]MIP1α | 0.03 | MIP1α | 0.1 |
| Histamine H$_1$ | [$^3$H]pyrilamine | 3 | pyrilamine | 1 |
| Histamine H$_2$ | [$^{125}$I]APT | 0.2 | tiotidine | 100 |
| MC4 | [$^{125}$I]NDP-α-MSH | 0.05 | NDP-α-MSH | 1 |
| Melatonin ML$_1$ | [$^{125}$I]iodomelatonin | 0.025 | melatonin | 1 |
| Muscarinic M$_1$ | [$^3$H]pirenzepine | 2 | atropine | 1 |
| Muscarinic M$_2$ | [$^3$H]AF-DX 384 | 2 | atropine | 1 |
| Muscarinic M$_3$ | [$^3$H]4-DAMP | 0.2 | atropine | 1 |
| Muscarinic M$_4$ | [$^3$H]4-DAMP | 0.2 | atropine | 1 |
| Muscarinic M$_5$ | [$^3$H]4-DAMP | 0.2 | atropine | 1 |
| Neurokinin NK$_1$ | [$^{125}$I][sar$^9$,met$^{11}$]-SP | 0.15 | [sar$^9$,met$^{11}$]-SP | 1 |
| Neurokinin NK$_2$ | [$^{125}$I]NKA | 0.1 | [nle$^{10}$]-NKA(4-10) | 10 |
| Neurokinin NK$_3$ | [$^3$H]SR 142801 | 0.2 | SB 222200 | 10 |
| Neuropeptide Y$_1$ | [$^{125}$I]peptide YY | 0.05 | NPY | 1 |
| Neuropeptide Y$_2$ | [$^{125}$I]peptide YY | 0.015 | NPY | 1 |
| Neurotensin NT$_1$ | [$^{125}$I][Tyr$^3$]-neurotensin | 0.02 | neurotensin | 1 |
| δ opioid (δ$_2$) | [$^3$H]DADLE | 0.5 | naltrexone | 10 |
| κ opioid | [$^3$H]U 69593 | 0.7 | naloxone | 10 |
| μ opioid | [$^3$H]DAMGO | 0.5 | naloxone | 10 |
| ORL1 opioid | [$^3$H]nociceptin | 0.2 | nociceptin | 1 |
| PACAP | [$^{125}$I]PACAP(1-27) | 0.02 | PACAP(1-27) | 0.1 |
| Purine P2X | [$^3$H]α,β-MeATP | 3 | α,β-MeATP | 10 |
| Purine P2Y | [$^{35}$S]dATPαS | 10 | dATPαS | 10 |
| Serotonin 5HT$_{1A}$ | [$^3$H]8-OH-DPAT | 0.5 | 8-OH-DPAT | 10 |
| Serotonin 5HT$_{1B}$ | [$^{125}$I]CYP | 0.1 | serotonin | 10 |
| Serotonin 5HT$_{2A}$ | [$^3$H]ketanserin | 0.5 | ketanserin | 1 |
| Serotonin 5HT$_{2C}$ | [$^3$H]mesulurgine | 1 | SB 242084 | 10 |
| Serotonin 5HT$_3$ | [$^3$H]BRL 43694 | 0.5 | MDL 72222 | 10 |
| Serotonin 5HT$_{5A}$ | [$^3$H]LSD | 1 | serotonin | 100 |
| Serotonin 5HT$_6$ | [$^3$H]LSD | 2 | serotonin | 100 |
| Serotonin 5HT$_7$ | [$^3$H]LSD | 4 | serotonin | 10 |
| Sigma receptor (ns) | [$^3$H]DTG | 8 | haloperidol | 10 |
| Somatostatin (ns) | [$^{125}$I][Tyr$^{11}$]-sst14 | 0.05 | sst14 | 0.3 |
| Vasopressin VIP$_1$ | [$^{125}$I]VIP | 0.04 | VIP | 0.3 |

Abbreviation used:
(ns) = non-selective

Once the ligand has been selected, it will likely be necessary to label to the ligand to that subsequently the amount bound to the chosen GPCR can be determined (although it may be possible to perform an assay without labelling the ligand, providing that a sensitive and accurate method of determining the amount of unbound ligand is available—for example it may be possible to use an ELISA assay to measure unbound ligand, and by inference calculate the amount of bound ligand). Appropriate methods of labelling the ligand vary depending on the nature of the ligand: small molecules may be most readily labelled with a radionuclide such as $^3$H, $^{14}$C or $^{35}$S; peptides may be most readily labelled with a co-synthetic biotin (and subsequently with labelled streptavidin), with fluorescent tags (such as fluorescein isothiocyanate) or with radionuclides (such as $^{125}$I-iodination of tyrosine residues in the peptide); proteins may be most readily labelled with fluorescent tags (such as fluorescein isothiocyanate) or with radionuclides (such as $^{125}$I-iodination of tyrosine residues in the protein).

The extent of the labelling (that is, the proportion of molecules in the sample bearing the label) must be sufficient that the amount of ligand binding to the receptor can be conclusively quantitated.

With these two components it is then possible to test whether the compounds of the invention modulate ligand binding to any given GPCR, using methods well known in the art. For example, in a series of tubes the membrane preparation is mixed with the radioligand at a concentration near to the affinity constant for the binding of the ligand to the chosen GPCR. In some tubes, the compound of the invention is also added at various concentrations. In yet other tubes a positive control inhibitor is added (which may be a large excess of the same ligand as the radioligand but in the absence of the radionuclide tag). Typically, three tubes would be prepared under each set of conditions. The tubes are then incubated, typically at between 4° C. and 37° C., more typically at room temperature for a period of time to allow an equilibrium to be reached between free and bound radioligand. Typically, this will take from between 20 minutes and 4 hours, and the period required for any given set of reaction conditions can be determined by methods well known in the art (for example, by performing a time-course experiment). Once equilibrium is achieved, it is necessary to determine the amount of radioliagnd bound. For example, the membrane-bound receptor (plus any bound radioligand) can be separated from free radioligand in solution by filtration through filters (such as GF/C filters treated with 1% polyethyleneimine). The filters may then be air-dried and subjected to scintillation counting to determine the fraction of the radioligand added which is now bound to the receptor.

Alternatively, the compounds of invention may be subjected to screening using commercially available receptor screening procedures (for example, the services offered by Cerep, 128 Rue Danton, Paris, France). Such services readily identify members of a library, such as the library provided for in the invention, which modulate ligand binding to one or more GPCRs.

Compounds identified as modulating ligand binding to one or more GPCRs using the methods outlined above will usually be full antagonists. However, it is necessary to perform functional assay in order to confirm the anatgonist properties of the compound. For example, depending on the GPCR and/or the ligand used certain second messenger signals will be stimulated (or inhibited) in order to transduce the signal that the ligand is present. Cells may show and increase (or a decrease) in the cellular concentration of cyclic adenosie monophosphate (cAMP), various phosphorylated inositol-containing compounds (including I(1,4,5)P3 and I(1,3,5)P3), calcium ions, polyadenosine or other intracellular messengers known in the art, in response to presentation of the ligand. Full antagonists will abrogate the change in intracellular messengers caused by the natural ligand(s), and have no effect in the absence of natural ligand. In marked contrast, full agonists will have no effect when added with the natural ligand(s), but mimic the changes in intracellular messengers caused by the natural ligand(s) when added in the absence of natural ligand. Some compounds, including compounds of the invention may be partial antagonists, partial agonists or mixed agonist/anatgonists depending on the pattern of effects on intracellular messengers. Despite the complex pharmacological definition of such compounds, they may have useful therapeutic properties in certain diseases, and a number of well established human pharmaceuticals are known to be partial agonists, partial antagonists or mixed agonist/antagonists at one or more GPCRs.

B: GPCR Agonism

It is inherently considerably more difficult to test for agonist activity than antagonist activity, particularly using high throughput screening techniques. The compounds of the invention are, therefore, likely to be particularly useful in the search for agonists than general lead discovery libraries because of the higher incidence of GPCR agonists among the library elements.

A test for a GPCR agonist, in principle, requires a cell or organ culture system which responds to a natural ligand of the chosen GPCR(s) with a desirable biochemical or physiological response. Examples of such a response include, but are not limited to, changes in intracellular messengers (such as cAMP, IP(1,4,5)P3, calcium ions or polyadenosine), changes in enzyme activity (such as activation of protein kinases, phosphatases, metabolic enzymes or transport proteins), changes in gene expression patterns, altered phagocytosis, altered protein secretion, altered rate of proliferation, contraction of muscle cells/tissue, neurotransmission and so forth. Since responses such as these are inherently more complex to measure than the binding of natural ligand(s) to chosen GPCRs, this is why assays for GPCR agonists are more challenging than for antagonists.

The general method required to test whether a compound of the invention is an agonist at one or more chosen GPCRs is well established in the art. Cells are exposed to various concentrations of the test compound, for example, by addition of the compound in a suitable vehicle (such as DMSO, ethanol or methanol) at various concentrations (for example, from about 0.1 nM to about 10 mM) in the cell culture medium for period of time (for example, from 1 minute to 48 hours, depending on the timecourse of the response to be measured), typically at 37° C. In parallel cells are also exposed to the natural ligand, and left unexposed to any additional compound(s) (as control cells). At the end of the incubation period, a response known in the art to occur in response to the natural ligand binding to the chosen GPCR(s) is measured. If the compound of the invention is an agonist at the chosen GPCRs, then the responses to the test compound (at certain concentrations) will be qualitatively similar to the response to the natural ligand.

Examples of suitable assay systems for agonists at particular GPCRs follow:

Somatostatin is an agonist at the sstr2 and sstr5 receptors such that it inhibits the secretion of growth hormone by isolated pituitary cells. To determine whether compounds of the invention are agonists at sstr2 and/or sstr5, rat pituitary cells are isolated and placed into culture. The cells are then incubated alone, or in the presence of somatostatin at 33 nM, or in the presence of the test compound(s) at various concentrations from about 0.1 nM to about 10 mM at 37° C. for 24 hours. At the end of the experiment, the cell culture medium is removed, clarified by centrifugation and subjected to an assay for growth hormone (GH), for example by performing a commercially available ELISA or radioimmunoassay. The cells exposed to somatostatin will have produced between 30% and 90% less GH than cells incubated alone. If the compound of the invention is an agonist at the somatostatin receptors, then the level of GH will be lower in the medium from cells exposed to the test compound (at least at certain concentrations) than in the medium from cells incubated alone. Typically, medium is collected from three replicate wells containing cells treated identically under each of the conditions of the experiment, so that an appropriate statistical test (such as an ANOVA or unpaired Student's t-test) can be used to demonstrate that the test compound produced a statistically significant reduction in GH secretion, and therefore likely possesses agonist activity at the chosen receptors, sstr2 and/or sstr5.

Endothelin-1 is a peptide which signals through the ET-A and/or ET-B receptor to cause vasoconstriction. To determine whether compounds of the invention are agonists at ET-A and/or ET-B, rings of human aorta (obtained from transplant donor hearts) can be put into organ culture. Rings are then exposed either to increasing concentrations of Endothelin-1 (from 0.01 nM to 100 nM), or to increasing concentrations of the test compound(s) (from about 0.1 nM to about 10 mM) at 37° C., raising the ceoncentration of the appropriate agent approximately every 5 minutes. Throughout the experiment the contraction of the aortic ring is measured by a strain guage designed and commercially available for such a purpose. The rings exposed to endothelin-1 will contract as the concentration of endothelin-1 is increased, so that by the time the top concentration is reached the force exerted on the strain guage will be significantly higher than prior to addition of endothelin-1. If the compound of the invention is an agonist at the endothelin receptors, then the force exerted on the strain guage will also be higher (at least at certain concentrations) than prior to addition of the test compound. Typically, three or more separate aortic rings are treated with increasing concentrations of the same agent under identical experimental conditions, so that an appropriate statistical test (such as an ANOVA or unpaired Student's t-test) can be used to demonstrate that the test compound produced a statistically significant increase in aortic contraction, and therefore likely possesses agonist activity at the chosen receptors, ET-A and/or ET-B The chemokine SDF-1a is a peptide which signals through the CXCR4 receptor to cause leukocyte migration. To determine whether compounds of the invention are agonists at CXCR4 cultured human immortalised T-cells (Jurkat T cells, for example), are placed in the top well of a purpose-built commercially available transwell migration apparatus. Replicate wells are then exposed to lower chambers containing only culture medium, or to lower chambers containing SDF-1a at 75 nM, or to lower chambers containing various concentrations of the test compound(s) (from about 0.1 nM to about 10 mM) and incubated for a period of time (typically between 30 minutes and 3 hours) at 37° C. At the end of the incubation, the number of cells present in the lower chamber is a measure of the amount of migration occurring. The number of cells in the lower chamber may be counted by direct visualisation, or by various well-known methods such as incubation with MTT dye which is converted to an insoluble blue formazan product in proportion to the number of cells present. In wells exposed to a lower chamber containing SDF-1a, the number of cells in the lower chamber will be between 2-fold and 10-fold higher than the number of cells in lower chambers containing culture medium alone. If the compound of the invention is an agonist at CXCR4, then the number of cells in the lower chambers containing the test compound(s) will also be higher (at least at certain concentrations) than in the lower chambers containing medium alone. Typically, three or more separate chambers are treated identically under each of the experimental conditions, so that an appropriate statistical test (such as an ANOVA or unpaired Student's t-test) can be used to demonstrate that the test compound produced a statistically significant increase in leukocyte migration, and therefore likely possesses agonist activity at the chosen receptors, ET-A and/or ET-B.

The bioactive amine adrenalin increases the intracellular concentration of cAMP in vascular smooth muscle cells. To determine whether compounds of the invention are agonists at β-adrenoreceptors, rat vascular smooth muscle cells from thoracic aorta are isolated and placed into culture. The cells are then incubated alone, or in the presence of the adrenalin agonist salbutamol at 33 nM, or in the presence of the test compound(s) at various concentrations from about 0.1 nM to about 10 mM at 37° C. for 15 minutes. At the end of the experiment, the cell culture medium is removed, the cells are washed three times in ice cold buffer and then lysed in an appripriate lysis buffer, prior to measurement of the intracellular concentration of cAMP, for example by performing a commercially available ELISA or radioimmunoassay. The cells exposed to salbutamol will have an intracellular cAMP concentration between 15% and 150% higher than cells exposed to medium alone. If the compound of the invention is an agonist at the β-adrenoreceptors, then the intracellular concentration of cAMP will be higher in the cells exposed to the test compound (at least at certain concentrations) than in the cells incubated alone. Typically, cell lysate is prepared from three replicate wells containing cells treated identically under each of the conditions of the experiment, so that an appropriate statistical test (such as an ANOVA or unpaired Student's t-test) can be used to demonstrate that the test compound produced a statistically significant increase in intracellular cAMP concentration, and therefore likely possesses agonist activity at the chosen β-adrenoreceptors.

It will be obvious that assays such as the examples above will identify agonists at the chosen GPCRs, and distinguish the compounds of the invention from inactive compounds and from compounds with antagonist or partial antagonist activity at the chosen GPCR, but will not necessarily uniquely identfy the chosen GPCR as the molecular target of the compound of the invention. For example, a compound of the invention demonstrated to elevate cAMP in vascular smooth muscle cells to the same extent as the β-adrenoreceptor agonist salbutamol, may be an agonist at the β-adrenoreceptor GPCRs, or it may be an agonist at another GPCR which also elevates cAMP (such as dopamine D2 receptor). Alternatively, a compound of the invention which stimulates the migration of leukocytes to a similar extent to SDF-1a may be an agonist at CXCR4, or it may be an agonist at another GPCR which stimulates leukocyte migration (such as the C5a receptor). Validation of the molecular target GPCR at which compounds of the invention act as an agonist will require the performance of additional experiments using specific antagonists already identified against the chosen GPCR, or the use of recombinant cell lines expressing only the chosen GPCR. For example, if the leukocyte migration induced by a compound of the invention were inhibited by the addition of the CXCR4-specific antagonist AMD3100 at an appropriate concentration, then it would be reasonable to conclude that CXCR4 was the molecular target of the compound of the invention. Similarly, if the leukocyte migration induced by a compound of the invention was observed using a cell line expressing CXCR4, but absent in the same cell line not expressing CXCR4, then it would be reasonable to conclude that CXCR4 was the molecular target of the compound of the invention.

The invention claimed is:

1. A compound of formula (I)

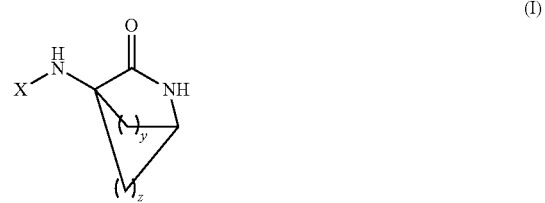

wherein:
y is any integer from 1 to 8;
z is any integer from 1 to 8 with the proviso that y and z cannot simultaneously be 1;
X is —CO—$(Y)_k$—$(R^1)_n$ or $SO_2$—$(Y)_k$—$(R^1)_n$;
k is 0 or 1;
Y is a cycloalkyl, polycyloalkyl, cycloalkenyl or polycycloalkenyl group;
each $R^1$ is independently selected from an alkylaminoalkyl, alkylaminodialkyl, charged alkylaminotrialkyl or charged alkylcarboxylate radical of 1 to 20 carbon atoms;
or each $R^1$ is independently selected from charged aminotrialkyl, or carboxylate radical; and
n is any integer from 1 to m, where m is the maximum number of substitutions permissible on the cyclo-group Y;
and, where $R^1$ is charged, one or more suitable counter-ions are present.

2. The compound of claim 1 wherein Y is an adamantyl, adamantanemethyl, bicyclooctyl, cyclohexyl, or cyclopropyl group.

3. A pharmaceutical composition comprising, as active ingredient, a compound of formula (I):

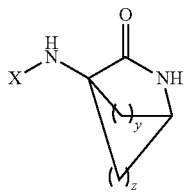

(I)

(II)

wherein y is any integer from 1 to 8;

z is any integer from 1 to 8 with the proviso that y and z cannot simultaneously be 1;

X is —CO—(Y)$_k$—(R$^1$)$_n$ or SO$_2$—(Y)$_k$—(R$^1$)$_n$;

k is 0 or 1;

Y is a cycloalkyl, polycyloalkyl, cycloalkenyl or polycycloalkenyl group;

each R$^1$ is independently selected from an alkylaminoalkyl, alkylaminodialkyl, charged alkylaminotrialkyl, or charged alkylcarboxylate radical of 1 to 20 carbon atoms;

or each R$^1$ is independently selected from charged aminotrialkyl, or carboxylate radical; and n is any integer from 1 to m, where m is the maximum number of substitutions permissible on the cyclo-group Y;

and, where R$^1$ is charged, one or more suitable counter-ions are present, or a pharmaceutically acceptable salt thereof, and at least one pharmaceutically acceptable excipient and/or carrier.

4. The compound of claim 1 wherein the R$^1$ radical has a key carbon that is the 2-position of a carbonyl-containing radical or the 1-position of a sulfonyl containing radical, which is di-substituted with the same or different groups selected from: alkyl, haloalkyl, alkoxy, haloalkoxy, alkenyl, alkynyl and alkylamino radicals.

5. The compound of claim 4 wherein the key carbon is chiral.

6. The compound of claim 4 wherein the key carbon has sp3 hybridised bonds.

7. The compound of claim 4 wherein the key carbon has essentially tetrahedral bond angles.

8. The compound of claim 4 wherein the ring or rings of Y constrain the bond angles at the key carbon to be essentially tetrahedral.

9. The compound of claim 1 wherein y and z are the same integer other than 1, whereby the α-aminobicyclolactam ring is non-chiral.

10. The compound of claim 1 wherein y and z are not the same integer, whereby the α-aminobicyclolactam ring is chiral.

11. The compound of claim 10 wherein z is 3 and y is 1 or 2 or 4-8, whereby the compound contains a lactam ring which is 7 membered.

12. The compound of claim 10 wherein z is 2 and y is 1 or 3-8, whereby the compound contains a lactam ring which is 6 membered.

13. A compound of formula (II)

wherein:

the bridge Q in formula (II) represents a bridging group independently selectable from the group consisting of alkenylene and alkylene substituted by halo, amino, aminoalkyl, aminodialkyl, charged trialkylamino, charged carboxylate or hydroxy moieties having a carbon chain length of from 1 to 8;

z is any integer from 1 to 8;

X is —CO—(Y)$_k$—(R$^1$)$_n$ or SO$_2$—(Y)$_k$—(R$^1$)$_n$;

k is 0 or 1;

Y is a cycloalkyl, polycyloalkyl, cycloalkenyl or polycycloalkenyl group;

each R$^1$ is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;

or each R$^1$ is independently selected from fluoro, chloro, bromo, iodo, hydroxy, oxyalkyl, amino, aminoalkyl, aminodialkyl, charged aminotrialkyl, or carboxylate radical; and n is any integer from 1 to m, where m is the maximum number of substitutions permissible on the cyclo-group Y; or alternatively R$^1$ may be a peptido radical having from 1 to 4 peptidic moieties linked together by peptide bonds; wherein the 1 to 4 peptidic moieties are selected from the 20 naturally occurring amino acids and, where one or more of R$^1$ and the bridging group is charged, one or more suitable counter-ions are present.

14. The pharmaceutical composition of claim 3 wherein Y is an adamantyl, adamantanemethyl, bicyclooctyl, cyclohexyl, or cyclopropyl group.

15. The pharmaceutical composition of claim 3 wherein the R$^1$ radical has a key carbon that is the 2-position of a carbonyl-containing radical or the 1-position of a sulfonyl containing radical, which is di-substituted with the same or different groups selected from: alkyl, haloalkyl, alkoxy, haloalkoxy, alkenyl, alkynyl and alkylamino radicals.

16. The pharmaceutical composition of claim 15 wherein the key carbon is chiral.

17. The pharmaceutical composition of claim 15 wherein the key carbon has sp3 hybridised bonds.

18. The pharmaceutical composition of claim 15 wherein the key carbon has essentially tetrahedral bond angles.

19. The pharmaceutical composition of claim 15 wherein the ring or rings of Y constrain the bond angles at the key carbon to be essentially tetrahedral.

20. The pharmaceutical composition of claim 3 wherein y and z are the same integer other than 1, whereby the α-aminobicyclolactam ring is non-chiral.

21. The pharmaceutical composition of claim 3 wherein y and z are not the same integer, whereby the α-aminobicyclolactam ring is chiral.

22. The pharmaceutical composition of claim 21 wherein z is 3 and y is 1 or 2 or 4-8, whereby the pharmaceutical composition contains a lactam ring which is 7-membered.

23. The pharmaceutical composition of claim 21 wherein z is 2 and y is 1 or 3-8, whereby the pharmaceutical composition contains a lactam ring which is 6-membered.

* * * * *